(12) United States Patent
McLaughlin

(10) Patent No.: US 10,973,939 B2
(45) Date of Patent: Apr. 13, 2021

(54) SYSTEM AND METHOD FOR ASEPTIC PACKAGING OF A DRUG DELIVERY DEVICE COMPONENTS

(71) Applicant: Insulet Corporation, Acton, MA (US)

(72) Inventor: Ian McLaughlin, Boxboro, MA (US)

(73) Assignee: INSULET CORPORATION, Acton, MA (US)

(*) Notice: Subject to any disclaimer, the term of this patent is extended or adjusted under 35 U.S.C. 154(b) by 186 days.

(21) Appl. No.: 16/053,231

(22) Filed: Aug. 2, 2018

(65) Prior Publication Data
US 2019/0038790 A1 Feb. 7, 2019

Related U.S. Application Data

(60) Provisional application No. 62/540,694, filed on Aug. 3, 2017.

(51) Int. Cl.
*B65B 3/00* (2006.01)
*B65B 55/04* (2006.01)
(Continued)

(52) U.S. Cl.
CPC ............ *A61L 2/206* (2013.01); *A61L 2/08* (2013.01); *A61L 2/26* (2013.01); *A61M 5/001* (2013.01);
(Continued)

(58) Field of Classification Search
CPC ........ B65B 55/04; B65B 55/10; A61M 5/001; A61M 5/002; A61M 5/008;
(Continued)

(56) References Cited

U.S. PATENT DOCUMENTS 2,833,007 A * 5/1958 Messer, Sr. ........... A61M 5/002
422/310
4,307,713 A 12/1981 Galkin et al.
(Continued)

FOREIGN PATENT DOCUMENTS

EP 2099384 A1 9/2009
ES 2559866 T3 2/2016
(Continued)

OTHER PUBLICATIONS

International Search Report and Written Opinion for PCT/US18/52468, dated Feb. 26, 2019, 16 pages.
(Continued)

*Primary Examiner* — Thanh K Truong
*Assistant Examiner* — Katie L Gerth
(74) *Attorney, Agent, or Firm* — Kacvinsky Daisak Bluni PLLC

(57) ABSTRACT

A method for sterilizing a drug delivery device may comprise disposing a liquid drug container, a needle conduit and a cap in a sterilization enclosure so that a mouth portion of the liquid drug container is registered with, and spaced apart from, a circumferential lip of the cap; disposing a cover over the liquid drug container, the needle conduit, and the cap, sealing the sterilization enclosure; subjecting the interior of the sterilization enclosure to a sterilization process in which the liquid drug container, the needle conduit, and the cap are exposed to the sterilization fluid and are sterilized; and applying a downward force to the liquid drug container to move the mouth portion into engagement with the circumferential lip of the cap and to snap the cap onto the liquid drug container to seal the cap and needle conduit to the liquid drug container in an assembled configuration.

14 Claims, 8 Drawing Sheets

(51) Int. Cl.
*B65B 55/10* (2006.01)
*A61L 2/20* (2006.01)
*A61M 39/18* (2006.01)
*A61M 5/142* (2006.01)
*A61M 5/28* (2006.01)
*A61L 2/08* (2006.01)
*A61L 2/26* (2006.01)
*A61M 5/00* (2006.01)

(52) U.S. Cl.
CPC ............ *A61M 5/002* (2013.01); *A61M 5/008* (2013.01); *A61M 5/14248* (2013.01); *A61M 5/288* (2013.01); *A61M 39/18* (2013.01); *B65B 3/003* (2013.01); *B65B 55/04* (2013.01); *B65B 55/10* (2013.01); *A61L 2202/121* (2013.01); *A61L 2202/122* (2013.01); *A61L 2202/23* (2013.01); *A61L 2202/24* (2013.01)

(58) Field of Classification Search
CPC ... A61M 5/14248; A61M 5/288; A61L 2/206; A61L 2/08; A61L 2/26; A61L 2202/23; A61L 2202/24; A61L 2202/122; A61L 2202/121
See application file for complete search history.

(56) References Cited

U.S. PATENT DOCUMENTS

| | | | |
|---|---|---|---|
| 4,416,663 A | 11/1983 | Hall | |
| 4,801,957 A | 1/1989 | Vandemoere | |
| 4,850,954 A | 7/1989 | Charvin | |
| 4,882,600 A | 11/1989 | Van de Moere | |
| 4,973,998 A | 11/1990 | Gates | |
| 5,045,871 A | 9/1991 | Reinholdson | |
| 5,239,326 A | 8/1993 | Takai | |
| 5,452,033 A | 9/1995 | Balling et al. | |
| 5,576,781 A | 11/1996 | Deleeuw | |
| 5,899,882 A | 5/1999 | Waksman et al. | |
| 6,164,044 A * | 12/2000 | Porfano | B65B 55/10 422/28 |
| 6,685,452 B2 | 2/2004 | Christiansen et al. | |
| 6,767,319 B2 | 7/2004 | Reilly et al. | |
| 7,182,726 B2 | 2/2007 | Williams et al. | |
| 7,303,073 B2 | 12/2007 | Raynal-Olive et al. | |
| 8,056,719 B2 | 11/2011 | Porret et al. | |
| 8,105,282 B2 | 1/2012 | Susi et al. | |
| 8,461,561 B2 | 6/2013 | Freeman et al. | |
| 8,727,117 B2 | 5/2014 | Maasarani | |
| 9,005,166 B2 | 4/2015 | Uber, III et al. | |
| 9,248,229 B2 | 2/2016 | Devouassoux et al. | |
| 9,427,710 B2 | 8/2016 | Jansen | |
| 9,555,911 B2 | 1/2017 | Pawlowski et al. | |
| 9,598,195 B2 | 3/2017 | Deutschle et al. | |
| 9,862,519 B2 | 1/2018 | Deutschle et al. | |
| 10,086,131 B2 | 10/2018 | Okihara | |
| 10,342,926 B2 | 7/2019 | Nazzaro et al. | |
| 2004/0139698 A1* | 7/2004 | Grifols Lucas | B65B 7/161 53/426 |
| 2006/0086909 A1 | 4/2006 | Schaber | |
| 2009/0254041 A1 | 10/2009 | Krag et al. | |
| 2014/0163664 A1 | 6/2014 | Goldsmith | |
| 2015/0057613 A1 | 2/2015 | Clemente et al. | |
| 2015/0078961 A1* | 3/2015 | Opie | A61L 2/26 422/28 |
| 2015/0196720 A1* | 7/2015 | Okihara | A61M 5/288 206/366 |
| 2016/0262984 A1* | 9/2016 | Arnott | A61J 1/1406 |

FOREIGN PATENT DOCUMENTS

| | | |
|---|---|---|
| GB | 2461086 A | 12/2009 |
| JP | 2002126039 A | 5/2002 |
| WO | 2017089289 A1 | 6/2017 |
| WO | 2017205816 A1 | 11/2017 |
| WO | 2018075851 A2 | 4/2018 |

OTHER PUBLICATIONS

International Search Report and Written Opinion for PCT/US2017/061095, dated Feb. 20, 2018, 8 pages.
International Preliminary Report on Patentability for the International Patent Application No. PCT/US2017/061095, dated May 23, 2019, 7 pages.
International Search Report and Written Opinion for PCT/US17/061095, dated Feb. 20, 2018, 8 pages.

* cited by examiner

SYSTEM AND METHOD FOR ASEPTIC PACKAGING OF A DRUG DELIVERY DEVICE COMPONENTS

PRIORITY

This application claims the benefit of priority under 35 U.S.C. § 119 to U.S. Provisional Patent Application Ser. No. 62/540,694, filed Aug. 3, 2017, which is incorporated by reference herein in its entirety and for all purposes.

TECHNICAL FIELD

The present application generally relates to medication delivery devices, and more particularly to systems and methods for sterilizing drug delivery devices.

BACKGROUND

Drug delivery devices can be provided to a user with a liquid drug pre-filled in a drug container of the device. As will be appreciated, portions of the devices that will be exposed to the liquid drug must be sterilized. When a device is sealed for intended use, (such as a sterile fluid path in a non-sterile device) the options for sterilization become limited. It may not be possible or practical to use gaseous methods such as Ethylene Oxide, steam, vaporized Hydrogen Peroxide, and the like due to the inability of such fluids to penetrate into the sealed environment. It may possible to use radiation or heat to sterilize internal volumes of the sealed device, but such options may not be technically feasible because radiation and heat can have deleterious effects on certain materials of the device. Alternatively, the device could be aseptically assembled, which would allow the individual components to be sterilized by any method and then assembled into a sealed system, however, such an approach may be cost prohibitive.

Thus, it would be desirable to have allow components of a drug delivery device to be sterilized using any of a variety of methods, while eliminating the need for costly aseptic assembly environments and equipment.

SUMMARY

The present disclosure in various embodiments includes systems and methods for aseptic packaging of drug delivery device components. In an embodiment, a method for sterilizing a drug delivery device may include disposing a liquid drug container, a needle conduit, and a cap in a sterilization enclosure so that a mouth portion of the liquid drug container may be registered with, and spaced apart from, a circumferential lip of the cap. A cover may be disposed over the liquid drug container, the needle conduit, and the cap, sealing the sterilization enclosure. An interior of the sterilization enclosure may be subjected to a sterilization process in which the liquid drug container, the needle conduit, and the cap may be exposed to a sterilization fluid and may be sterilized. The interior of the sterilization enclosure may be subjected to a sterilization process that may sterilize respective interior portions of the liquid drug container, the needle conduit, and the cap. A downward force may be applied to the liquid drug container to move the mouth portion into engagement with the circumferential lip of the cap and may snap the cap onto the liquid drug container to seal the cap and the needle conduit to the liquid drug container in an assembled configuration. The downward force may be applied to a cover disposed over the enclosure. The applied downward force may move the needle conduit through a cap seal disposed in the cap, but may not move the needle through a container seal disposed in the container. The sterilization enclosure may be unsealed. A fluid assembly comprising the liquid drug container, the needle conduit, and the cap may be removed. A liquid drug may be supplied to the liquid drug container. A plunger may be disposed into the liquid drug container, sealing the liquid drug within the liquid container. A first tray may be disposed into the enclosure below the cap and the liquid drug container. A second tray may be disposed into the enclosure and may be configured to hold the liquid drug container. The liquid drug container, the needle conduit, and the cap may be enclosed in a radiation shield. A seal may be disposed within the cap, extending out of the cap, and extending through the radiation shield. The needle may be pierced through the seal. The seal may be crimped to the liquid drug container such that they abut each other. The interior of the sterilization enclosure may be subjected to a sterilization process comprising radiation. The cap may be locked to the liquid drug container.

In an aspect, a system for sterilizing a drug delivery device may include an enclosure. A first tray may be disposed within the enclosure. A second tray may be disposed within the enclosure. A cap may be disposed on the second tray. A needle conduit may extend from the cap. A liquid drug container may be disposed on the second tray such that a mouth portion of the liquid drug container may be registered with, and spaced apart from, a circumferential lip of the cap. A flexible cover may be disposed on the enclosure having a protrusion configured to substantially align with the liquid drug container. A plunger may be disposed within the liquid drug container configured to seal a liquid drug within the container. A container seal may be disposed within the liquid drug container. A cap seal may be disposed within the cap. The liquid drug container and the cap may assume a locked configuration when the mouth portion of the container that may be pressed against the circumferential lip of the cap. The needle conduit may extend through a cap seal disposed within the cap at a first end and may extend into a cannula at a second end.

In an aspect, a system for sterilizing a drug delivery device via radiation may include a liquid drug container. A liquid drug may be disposed within the container. A radiation shield may be disposed about the liquid drug container. A cap may be about an end of the liquid drug container. A seal may be disposed within the cap, may be coupled to the liquid drug container, and may extend out of the cap and through the radiation shield. A needle conduit may be registered with, and spaced apart from, a portion of the seal extending through the radiation shield. The needle conduit may be configured to extend through the seal and into the liquid drug container upon application of a force onto the needle conduit. The seal may comprise rubber. The liquid drug container may comprise glass. The seal may be coupled against the liquid drug container. A sterilization enclosure and a cover may be disposed about the radiation shielding and needle conduit. The cover may comprise a flexible cover having a protrusion configured to substantially align with the needle conduit and the liquid drug container.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

Figure 1:
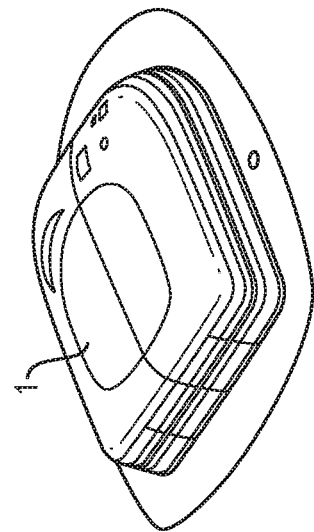
FIG. 1 illustrates a perspective view of a drug delivery device, in accordance with an embodiment of the present disclosure.

The present disclosure is not limited to the particular embodiments described. The terminology used herein is for the purpose of describing particular embodiments only, and is not intended to be limiting. Unless otherwise defined, all technical terms used herein have the same meaning as commonly understood by one of ordinary skill in the art to which the disclosure belongs.

As used herein, the singular forms "a," "an," and "the" are intended to include the plural forms as well, unless the context clearly indicates otherwise. The terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

This disclosure presents various systems, components, and methods related to drug delivery devices. Each of the systems, components, and methods disclosed herein provides one or more advantages over conventional systems, components, and methods.

The disclosure contemplates performing a final assembly of a device inside a sterilization container such as, e.g., a tub, bag, custom fixture, etc. The final assembly step will provide the means to convert the device from "open", e.g., with internal portions of the device exposed to the external atmosphere, to "closed", e.g., with internal portions of the device not exposed to the external atmosphere. Converting a device from an "open" configuration to a "closed" configuration may be accomplished by snapping together shells, plugging a hole, capping a hole, closing a flap or door, or the like. In all cases the device will be "open" prior to and during sterilization, and then "closed" while still inside a sterile packaging. The closing step can be performed in any of a variety of ways, including through the use of mechanical manipulation of the packaging, magnetics to manipulate the device or packaging, and/or electromechanical activation (e.g., applying power through wireless charging, solar power, or activating electrical components). This disclosure provides disposable or reusable aseptic environments in which to perform the final assembly of sterilized device components without the added risks associated with breaching an aseptic environment to introduce parts.

In various embodiments, described here or otherwise, within the scope of the present disclosure, the device arrangements and methods may be applied to sub-assemblies as well as complete drug delivery devices. In the case of a pre-filled drug delivery device, the drug may not be compatible with a preferred or any sterilization method. In such a case a sealed fluid path may be attached to a drug container and sterilized prior to filling. The fluid path may remain open during sterilization and may be sealed prior to or after filling the drug container with a liquid drug and assembled into a final device, thereby maintaining the sterility and integrity of the fluid path while allowing for the use of more sterilization modalities than a filled and/or sealed device. The sealed and sterile fluid path may be filled and assembled into a final device providing a pre-filled device with a sterile fluid path, and without risk of damaging the drug that could be caused by sterilizing the fluid path after filling.

The disclosed systems and methods address issues relating to device sterilization and providing a device that is pre-filled with a liquid drug. The disclosed systems and methods facilitate aseptic filling of a terminally sterilized drug delivery device, resulting in a terminally sterilized pre-filled device. As mentioned, one problem with providing a pre-filled drug delivery device may be that it can be difficult or impossible to sterilize the pre-filled device without damaging the liquid drug, because conventional sterilization processes may require heat, radiation, or chemicals, all of which may be capable of damaging the drug.

Figure 2:
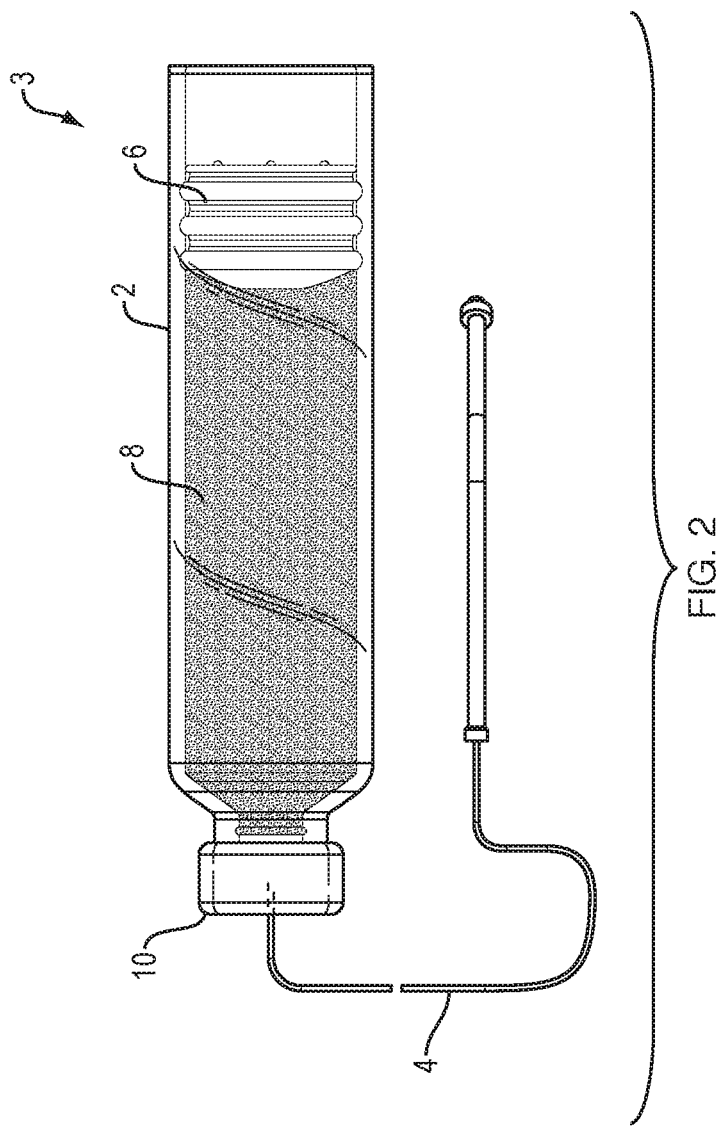
FIG. 2 illustrates a partial transparent view of an exemplary fluid assembly, in accordance with an embodiment of the present disclosure.

With reference to FIGS. 1 and 2, an embodiment of a drug delivery device 1 may be an OmniPod® (Insulet Corporation, Billerica, Mass.) insulin delivery device in some embodiments. The drug delivery device 1 may include a fluid assembly 3 (see FIG. 2), which includes a liquid drug container 2, a cap 10 sealing the container 2 at a first end, a needle conduit 4 coupled to the cap 10, and also sealed by a plunger 6 at an opposite, second, end of the container 2. The fluid assembly 3 of FIG. 2 is illustrated in a closed, assembled configuration. A quantity of liquid drug 8 may be disposed within the liquid drug container 2. A cap 10 may be coupled to the first end of the liquid drug container 2 and the needle conduit 4 may pass through the cap 10. The needle conduit 4 extending through the cap 10 may provide a fluid path for the drug 8 out of the container 2. The plunger 6 may move as fluid is supplied to or egressed from the container 2. The plunger 6 may vary its position to control a volume of the fluid drug 8 within the container 2. It will be appreciated that the position will be variable based on a desired fill volume of fluid drug 8 in the container 2. Any of the fluid arrangements disclosed herein, including any of the drug delivery systems disclosed herein, can be part of a wearable or on-body drug delivery device or pump, such as an Omni-Pod® (Insulet Corporation, Billerica, Mass., USA) device and/or any of the drug delivery devices described in U.S. Pat. Nos. 7,303,549; 7,144,384; 7,137,964; 6,960,192; 6,740,059; 6,699,218; 9,402,950; 7,771,412; 7,029,455; 6,740,05; and 6,656,159, each of which is incorporated herein by reference in its entirety and for all purposes.

Figure 4:
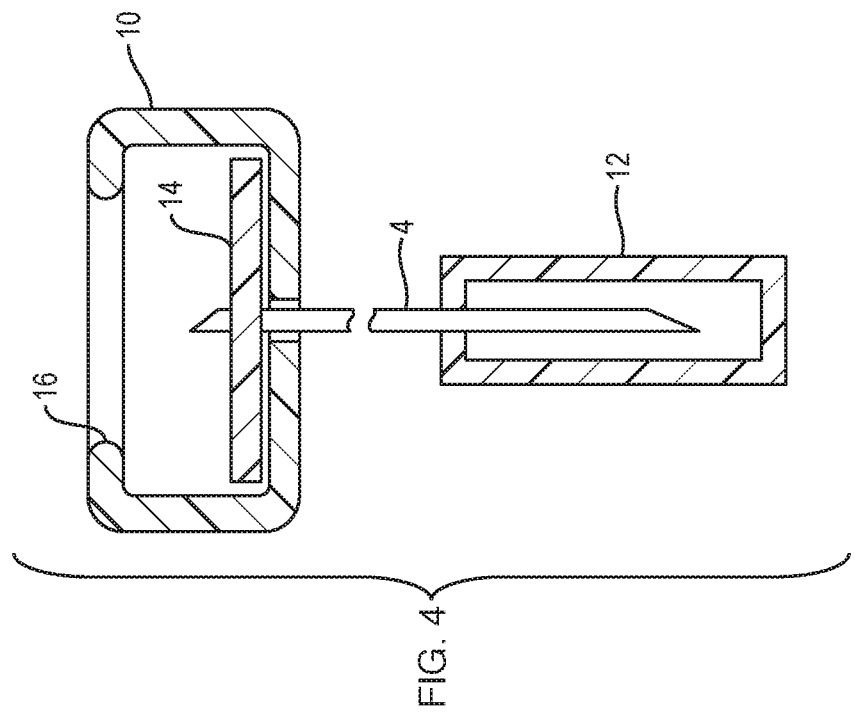
FIG. 4 illustrates a cross-section view of an exemplary cap, needle conduit, and cannula assembly, in accordance with an embodiment of the present disclosure.
Figure 3:
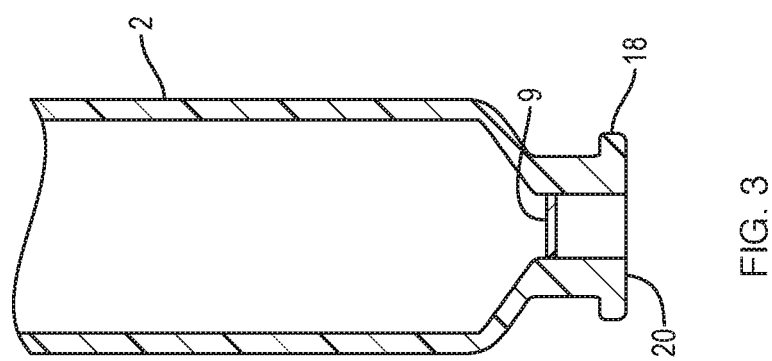
FIG. 3 illustrates a cross-section view of an exemplary liquid drug container, in accordance with an embodiment of the present disclosure.

With reference to FIGS. 3 and 4, a fluid assembly may be in a partially disassembled configuration. In this configuration, a liquid drug container 2 is not coupled to a cap 10 nor a plunger. A cap seal 14 is disposed within the cap 10, sealing an end of the cap 10 while the opposing end of the cap 10 is open. The needle conduit 4 is coupled at a first end to the cap 10 through the cap seal 14, and is also coupled to a cannula 12 at an opposite, second end. In this configuration the container is sealed by a container seal 9 disposed in a neck portion of the container 2 at one end, but the container 2 is open and is not sealed by a plunger at an opposing end.

In various embodiments, the cap 10 may have an inwardly protruding circumferential lip 16 that is configured to engage a corresponding circumferential shoulder 18 disposed on a mouth portion 20 of the liquid drug container 2. When the cap 10 is aligned with, and pressed against the mouth portion 20 of the container 2, the circumferential lip 16 flexes outwardly to pass over the shoulder 18, and then flexes inwardly once the lip 16 passes the shoulder 18 such that the fluid assembly assumes an assembled, locked configuration (e.g., FIG. 2). In the assembled configuration, the cap seal 14 disposed in the cap 10 seals against the mouth portion 20 of the liquid drug container 2.

Figure 5:
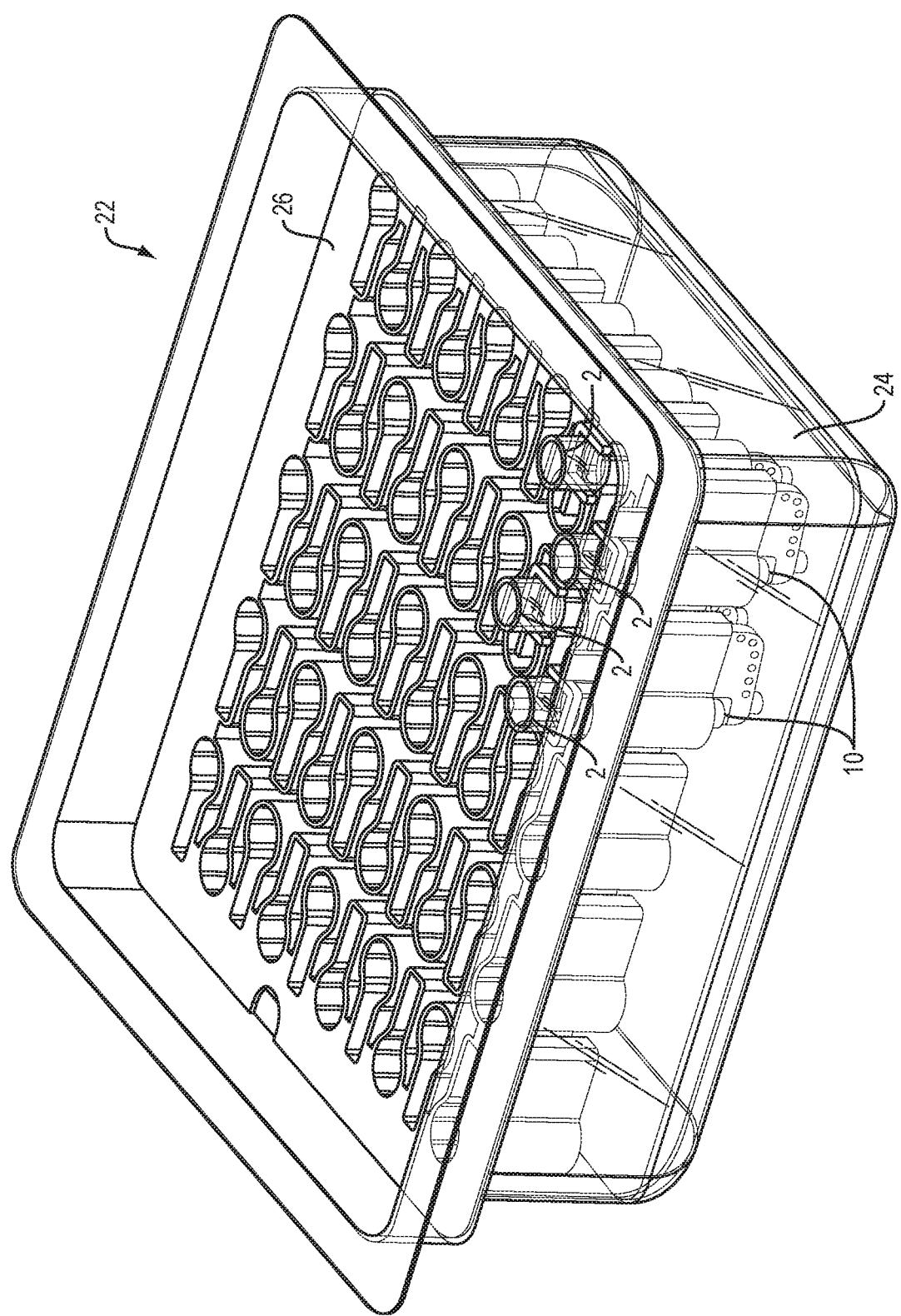
FIG. 5 illustrates an isometric view of an exemplary sterilization enclosure containing a plurality of liquid drug container, cap, needle conduit, and cannula assemblies, in accordance with an embodiment of the present disclosure.
Figure 6:
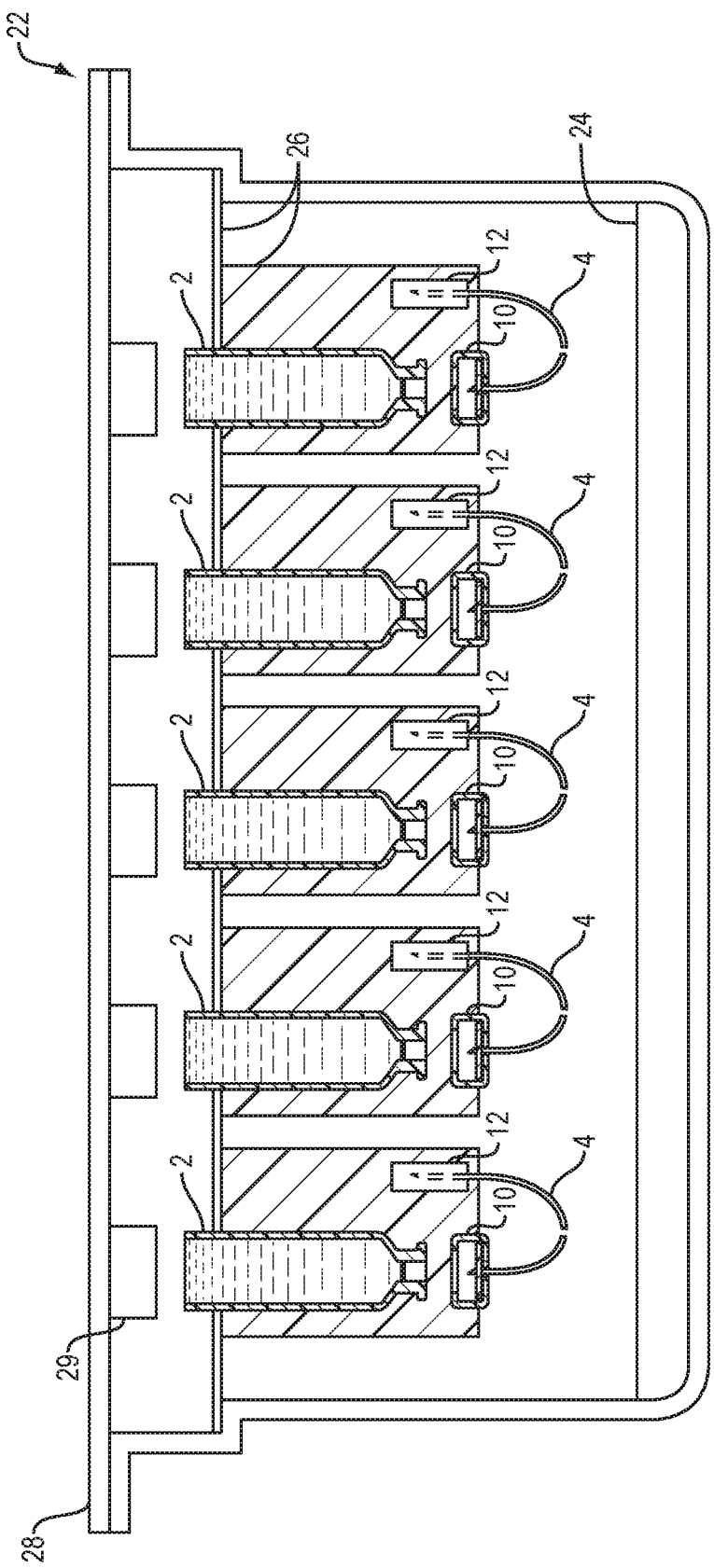
FIG. 6 illustrates a cross-section view of an exemplary sterilization enclosure in accordance with an embodiment of the present disclosure.

With reference to FIGS. 5 and 6, a liquid drug container 2, a needle conduit 4, and a cap 10 may be positioned within an exemplary sterilization enclosure 22 (e.g., a tub). FIG. 5 illustrates an arrangement in which multiple sets of fluid assemblies (i.e., liquid drug containers 2, needle conduits 4, and caps 10) can be sterilized together. A first tray 28 is disposed in a bottom portion of the enclosure 22 and a second tray 26 is disposed in a top portion of the enclosure 22. The cap 10 and needle conduit 4 are disposed on the second tray 26, however, the cap 10, needle conduit 4, and container 2 may be snap fit into the first 24 or second 26 tray. The liquid drug container 2 is disposed on the second tray 26 such that a mouth portion of the liquid drug container 2 is registered with, and spaced apart from, a circumferential lip of the cap 10. A cover 28 is disposed on the enclosure 22 having protrusions 29, and each protrusion 29 may be configured to substantially align with a liquid drug container 2. As illustrated in FIG. 6, the interiors of the liquid drug container 2, needle conduit 4, cap 10, and cannula 12 are exposed to the atmosphere of the sterilization enclosure 22. After the components within the enclosure 22 have undergone a sterilization process, a forced may be exerted on the cover 28 such that one or more protrusions exert a force onto a respective container 2. The force on the container 2 may move the mouth portion of the container 2 into engagement with the circumferential lip of the respective cap 10, snapping the cap 10 onto the liquid drug container 2 to seal the cap 10 and the needle conduit 4 to the liquid drug container 2 in an assembled configuration. The first tray 24 and/or second tray 26 may hold the cap and/or needle conduit 4 in place for the top tray 26 to force and snap the container 2 into the cap 10. The first tray 24 and/or the bottom of the enclosure 22 may act as a backstop for the container 2 to be forced and snapped into the cap 10. The first tray 28 or the bottom of the enclosure 22 may hold and align the cap10 and/or needle assembly with the second tray 26 and/or the contents held in the second tray. Various alignment geometries may be incorporated into the trays 24 and 26, the cover 28, and/or the enclosure 22.

Figure 7:
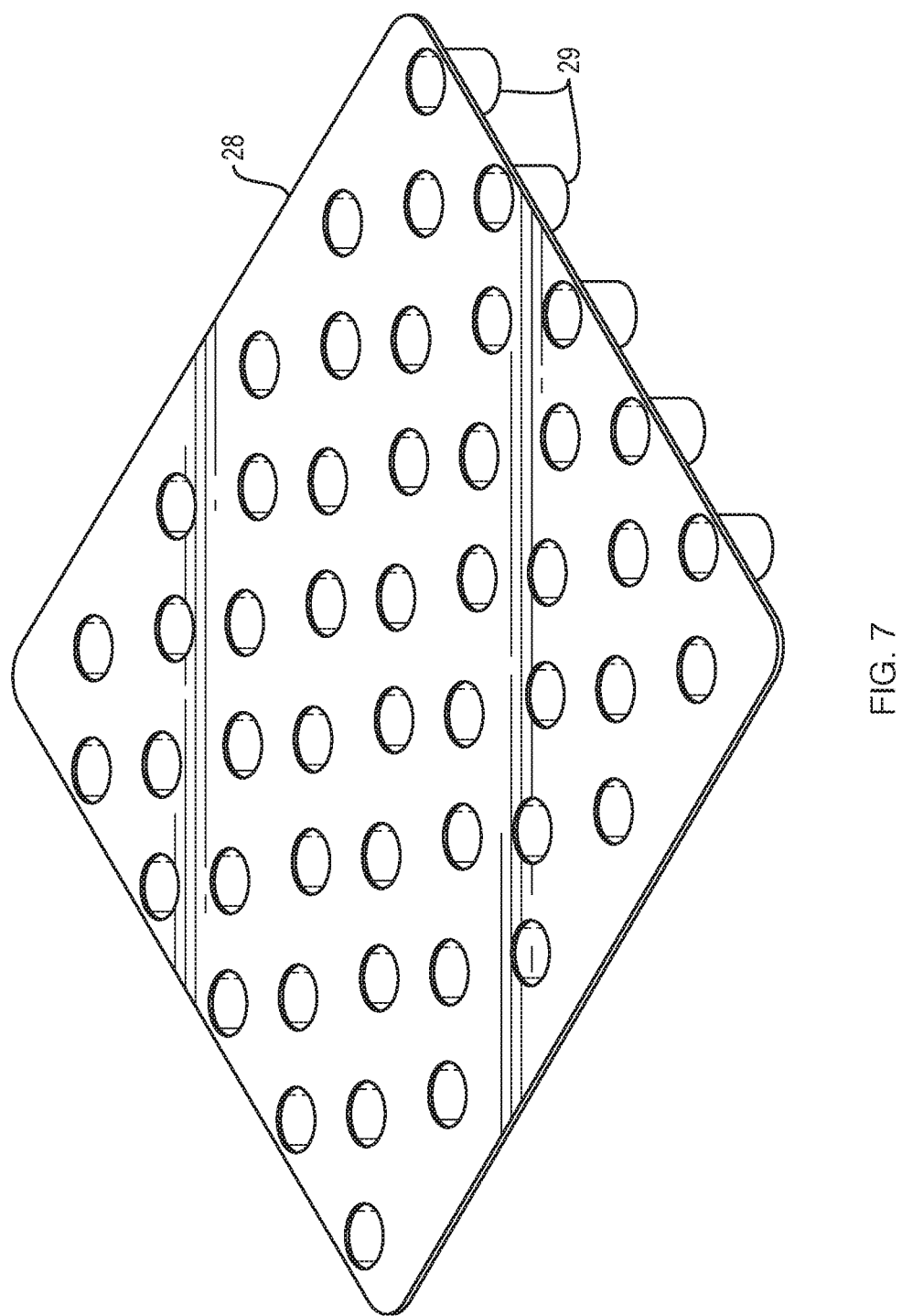
FIG. 7 illustrates an isometric view of an exemplary cover for use with the sterilization enclosure of FIGS. 5 and 6, in accordance with an embodiment of the present disclosure.

With reference to FIG. 7, a cover 28 for a sterilization enclosure 22 may include a plurality of protrusions 28 for aligning with individual liquid drug containers 2 within the sterilization enclosure 22. The protrusions 29 may be staggered in rows and/or columns such that they may align with respective containers 2 of fluid assemblies disposed within the enclosure 22. The cover 28 and/or the protrusions 29 may be flexible. In various embodiments, the cover 28 may seal the sterilization enclosure 22. Alternatively, an additional sealing element (such as a Tyvek® seal, which is not shown) may seal the sterilization enclosure 22. The cover 28 may be bonded to the tub and may allow a sterilizing agent, e.g., gas and/or vapor) through the cover 28, but not other materials, e.g., microbes, molds, spores, or the like, so the tub may remain sterile until 28 is removed.

Figure 8:
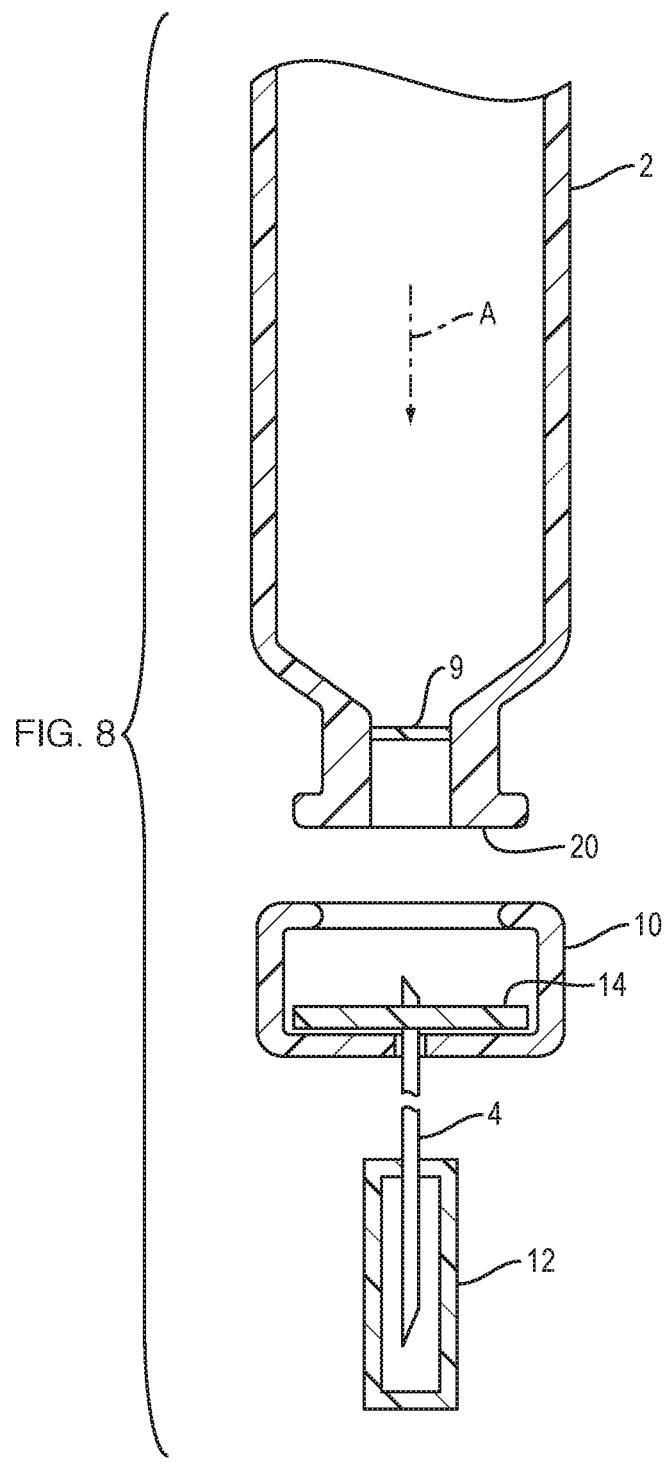
FIG. 8 illustrates a cross-section view of an exemplary cap, needle conduit and cannula assembly in a pre-engaged position in accordance with an embodiment of the present disclosure.

In various embodiments, the liquid drug container 2, needle conduit 4, cap 10, and cannula 12 may be held within the sterilization enclosure 22 within zero, one, or more trays (e.g., 24 and 26 of FIGS. 5 and 6) and subjected to one or more sterilization steps using any of a variety of sterilization techniques. For example, a sterilization technique may include evacuating the sealed sterilization enclosure 22, and then introducing a sterilization gas. With reference to FIGS. 6 and 8, once the sterilization is complete, the cover 28 (or other element) may be pressed downward, which may cause the liquid drug container 2 to move downward (in the direction of arrow "A") to engage the cap 10 and to snap the cap 10 into engagement with the mouth 20 of the liquid drug container 2 (see FIG. 8). In this manner, the sterilized cap 10 and needle conduit 4 can be assembled to the liquid drug container 2 within the sterile environment of the sterilization enclosure 22. The liquid drug container 2 may then be filled with liquid drug. In various embodiments, a fluid assembly in an assembled configuration may have the needle conduit 4 extending through the cap seal 14 and into the container 2 such that it is in fluid communication with the drug 8. Alternatively, the needle conduit 4 may extend into the cap 10 such that it is not in fluid communication with the drug 8 in the assembled configuration. In this configuration, the needle conduit 4 would not extend through the container seal 9 that is disposed within the container 2 (e.g., within a neck of the container 2). Once filled, the container seal 9 is between the end of the needle conduit 4 and the drug (e.g., the drug 8 in FIG. 2) in this assembled configuration. The needle conduit 4 may be driven into the container seal 9 by a motor of the device and/or by a user.

Figure 9:
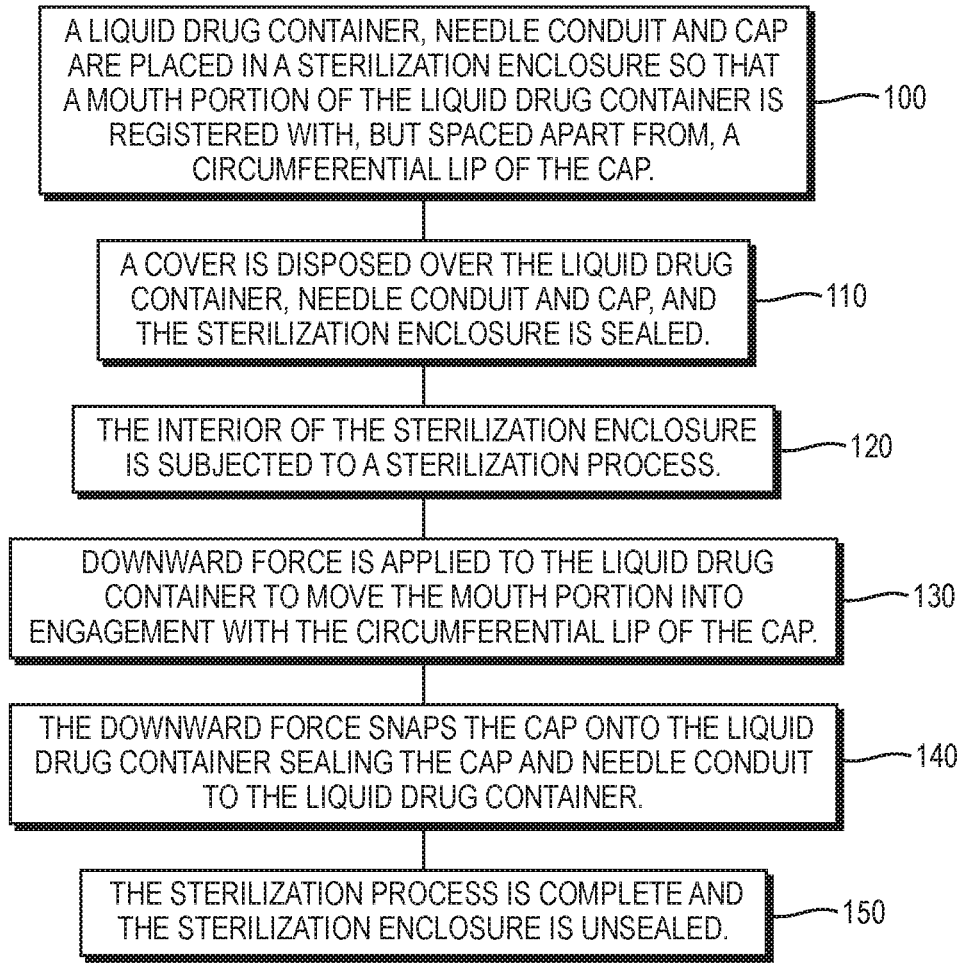
FIG. 9 is a flow diagram illustrating an example method, in accordance with an embodiment of the present disclosure.

With reference to FIG. 9, an embodiment of a method according to the present disclosure will be described. At step 100, a liquid drug container 2, needle conduit 4, and cap 10 are placed in a sterilization enclosure 22 such that a mouth portion 20 of the liquid drug container 2 is registered with (e.g., substantially aligned with, oriented towards, or the like), but spaced apart from, a circumferential lip 16 of the cap 10. A first tray 24 may be disposed into the enclosure 22 below the cap 10 and the liquid drug container 2. A second tray 26 may be disposed into the enclosure 22 configured to hold the liquid drug container 2 and/or the cap 10. The liquid drug container 2 may have a container seal 9 disposed in a neck portion of the container 2. At step 110, the cover 28 is disposed over the liquid drug container 2, needle conduit 4, and cap 10, and the sterilization enclosure 22 is sealed. At step 120, the interior of the sterilization enclosure 22 is subjected to a sterilization process, which in one non-limiting exemplary embodiment, is an ethylene oxide (EO) sterilization process. During this sterilization process the interior portions of the liquid drug container 2, needle conduit 4, cap 10, and cannula 12 are subjected to the sterilization fluid and are sterilized. At step 130, downward force is applied to the liquid drug container 2 to move the mouth portion 20 into engagement with the circumferential lip 16 of the cap 10. In some embodiments, the downward force is applied by a user, a robot, or other means to the cover 28. At step 140, the downward force snaps the cap 10 onto the liquid drug container 2 sealing the cap and needle conduit 4 to the liquid drug container 2. The downward force may move the needle conduit 4 through a cap seal 14 disposed in the cap 10, but not through the container seal 9 disposed in the container 2. A space between the seal 9, the cap 10, the needle conduit 4 and the cannula 12 remains sterilized and sealed from the environment. At step 150, the sterilization process is complete and the sterilization enclosure 22 is unsealed. A drug may be supplied to the liquid drug container 2. A plunger 6 may be disposed into the liquid drug container 2, sealing the liquid drug within the liquid container2. The assembled liquid drug container 2, needle conduit 4, and cap 10 may be removed from the enclosure 22.

Figure 10:
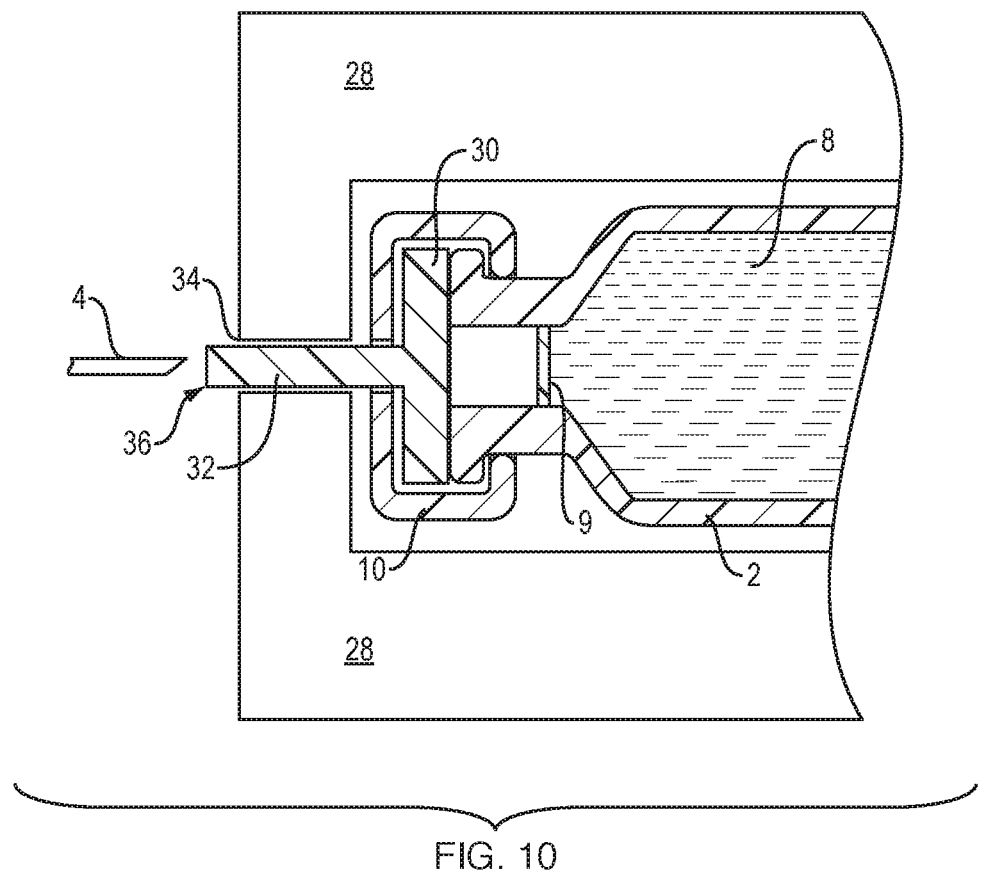
FIG. 10 illustrates a sterilization arrangement for a drug delivery device, in accordance with an embodiment of the present disclosure.
Figure 11:
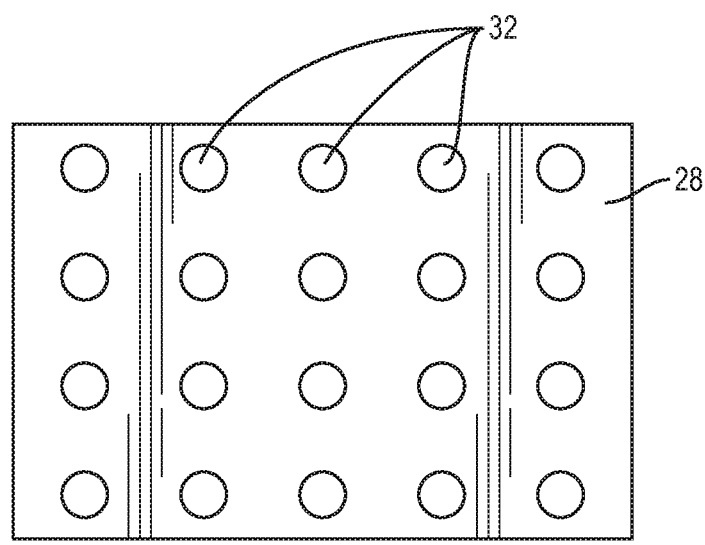
FIG. 11 illustrates a top view of an exemplary sterilization enclosure, in accordance with an embodiment of the present disclosure.

With reference to FIG. 10, an embodiment of a device according to the present disclosure may be configured for a radiation sterilization technique that may sterilize a portion of a drug delivery device while protecting a liquid drug 8 contained within the liquid drug container 2. Radiation shielding 28 is disposed about the liquid drug container 2 (which contains liquid drug 8). A cap 10 (e.g., a crimp cap) engages a seal 30 to couple the seal to the liquid drug container. A protruding portion 32 of the seal 30 may extend through an opening 34 in the shielding 28 such that only an end 36 of the protruding portion 32 is exposed to radiation during the sterilization procedure. The needle conduit 4 and associated components (e.g., a cannula) may be exposed to radiation and sterilized thereby in an open, unassembled configuration. The needle conduit 4 may then move into and through the seal 30 into a closed, assembled configuration, that may or may not extend into and through a container seal 9. It will be appreciated that multiple assemblies could be loaded in a sterilization enclosure such that the protruding portions 32 of the multiple assemblies protrude through the shielding (see FIG. 11), the group would be irradiated together Certain embodiments of the present disclosure are described herein. It is, however, expressly noted that the present disclosure is not limited to these embodiments, but rather the intention is that additions and modifications to what is expressly described herein are also included within the scope of the disclosure. Moreover, it is to be understood that the features of the various embodiments described herein are not mutually exclusive and can exist in various combinations and permutations, even if such combinations or permutations are not made express herein, without departing from the spirit and scope of the disclosure. In fact, variations, modifications, and other implementations of what is described herein will occur to those of ordinary skill in the art without departing from the spirit and the scope of the disclosure. As such, the disclosure is not to be defined only by the illustrative description.

What is claimed is:

1. A method for sterilizing a drug delivery device comprising:
   disposing a liquid drug container, a cap, and a needle conduit, wherein the needle conduit is separate from the liquid drug container, coupled to the cap and extending from the cap in a sterilization enclosure so that a mouth portion of the liquid drug container is registered with, and spaced apart from, a circumferential lip of the cap;
   disposing a cover over the liquid drug container, the needle conduit, and the cap, sealing the sterilization enclosure; and
   subjecting an interior of the sterilization enclosure to a sterilization process in which the liquid drug container, the needle conduit, and the cap are exposed to a sterilization fluid.

2. The method of claim 1, wherein the subjecting the interior of the sterilization enclosure to the sterilization process further comprises:
   sterilizing respective interior portions of the liquid drug container, the needle conduit, and the cap.

3. The method of claim 1, further comprising:
   applying a downward force to the liquid drug container to move the mouth portion into engagement with the circumferential lip of the cap and to snap the cap onto the liquid drug container to seal the cap and the needle conduit to the liquid drug container in an assembled configuration.

4. The method of claim 3, wherein the applying the downward force comprises applying the downward force to a cover disposed over the enclosure.

5. The method of claim 3, wherein applying the downward force moves the needle conduit through a cap seal disposed in the cap, without the needle conduit being moved through a container seal disposed in the container.

6. The method of claim 3, further comprising:
unsealing the sterilization enclosure; and
removing a fluid assembly comprising the liquid drug container, the needle conduit, and the cap.

7. The method of claim 6, further comprising:
supplying a liquid drug to the liquid drug container.

8. The method of claim 7, further comprising:
disposing a plunger into the liquid drug container, sealing the liquid drug within the liquid container.

9. The method of claim 1, further comprising:
disposing a first tray into the enclosure below the cap and the liquid drug container; and
disposing a second tray into the enclosure configured to hold the liquid drug container.

10. A method for sterilizing a drug delivery device comprising:
disposing a liquid drug container, a needle conduit, and a cap in a sterilization enclosure so that a mouth portion of the liquid drug container is registered with, and spaced apart from, a circumferential lip of the cap, wherein the cap:
is coupled to the needle conduit, which extends from the cap, and is separate from the liquid drug container;
disposing a cover over the liquid drug container, the needle conduit, and the cap, sealing the sterilization enclosure;
subjecting an interior of the sterilization enclosure to a sterilization process in which the liquid drug container, the needle conduit, and the cap are exposed to a sterilization fluid; and
applying a downward force to the liquid drug container to move the needle conduit through a cap seal disposed in the cap, without the needle conduit being moved through a container seal disposed in the liquid drug container.

11. The method of claim 10, further comprising:
disposing a first tray into the enclosure below the cap and the liquid drug container; and
disposing a second tray into the enclosure configured to hold the liquid drug container.

12. The method of claim 10, further comprising:
unsealing the sterilization enclosure; and
removing a fluid assembly comprising the liquid drug container, the needle conduit, and the cap.

13. The method of claim 12, further comprising:
supplying a liquid drug to the liquid drug container.

14. The method of claim 13, further comprising:
disposing a plunger into the liquid drug container, sealing the liquid drug within the liquid drug container.

* * * * *